United States Patent
Matsumoto et al.

[11] Patent Number: 6,087,530
[45] Date of Patent: Jul. 11, 2000

[54] PROCESS FOR PREPARING β-AMINO-α-HYDROXY ACID DERIVATIVES

[75] Inventors: Shingo Matsumoto; Kazuhiko Matsuo, both of Himeji; Tadashi Sugawa, Akashi; Tadashi Moroshima; Kenji Inoue, both of Kakogawa, all of Japan

[73] Assignee: Kaneka Corporation, Osaka, Japan

[21] Appl. No.: 09/437,426

[22] Filed: Nov. 15, 1999

Related U.S. Application Data

[62] Division of application No. 09/242,358, May 14, 1999, Pat. No. 6,020,518.

[30] Foreign Application Priority Data

Aug. 16, 1996 [JP] Japan ......... 8-234728

[51] Int. Cl.$^7$ .......... C07B 57/00; C07C 229/12; C07C 229/06; C07C 229/14
[52] U.S. Cl. .......... 562/402; 560/29; 562/422; 562/430; 562/444
[58] Field of Search ............ 560/29; 562/402, 562/430, 444, 422

[56] References Cited

U.S. PATENT DOCUMENTS

| | | | |
|---|---|---|---|
| 5,395,962 | 3/1995 | Kawashima | 562/401 |
| 5,510,520 | 4/1996 | Kawashima | 562/401 |
| 6,008,403 | 12/1999 | Katsuura et al. | 560/40 |

OTHER PUBLICATIONS

Database Caplus on STN, Acc. No. 1980:639932, Umezawa et al., (2S, 3R)—and (2R, 3R)–d–amino–2–hydroxy–5–methylhexanoic acid and their derivatives. JP 55076847 A2 (Abstract), 1980.

Database Caplus on STN, Acc. No. 1968:22222, Okai et al., 'Resolution of amino acids. VIII. Preparation of the four optical isomers of beta–hydroxyaspartic acid.' Bull. Chem. Soc. Jpn. (1967), 40(9), pp. 2154–2159 (Abstract), 1968.

*Primary Examiner*—Johann Richter
*Assistant Examiner*—Brian J. Davis
*Attorney, Agent, or Firm*—Pollock, Vande Sande & Amernick

[57] ABSTRACT

An object of the present invention is to provide a process for producing a β-amino-α-hydroxy acid derivative via efficient and industrially utilizable steps.

The present invention provides a process for producing a β-amino-α-hydroxy acid derivative represented by the general formula (2) given below which comprises hydrolyzing an α-amino-α', α-dihaloketone derivative of the general formula (1) given below in the presence of a base, followed by protecting the amino group or without protecting the same.

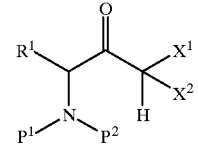

(1)

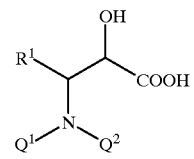

(2)

22 Claims, No Drawings

6,087,530

PROCESS FOR PREPARING β-AMINO-α-HYDROXY ACID DERIVATIVES

CROSS-REFERENCE TO RELATED APPLICATION

This application is a divisional of U.S. patent application Ser. No. 09/242,358 filed May 14, 1999 now U.S. Pat. No. 6,020,518 which is the national phase of PCT/JP97/02844 filed Aug. 18, 1997.

TECHNICAL FIELD

The present invention relates to a process for producing a β-amino-α-hydroxy acid derivative by the hydrolysis, in the presence of a base, of an α-amino-α', α'-dihaloketone derivative derived from the corresponding α-amino acid. More minutely, the present invention relates to a process for producing an optically active β-amino-α-hydroxycarboxylic acid derivative which comprises deriving an optically active α-amino acid, such as L-phenylalanine, into an α-amino-α', α'-dihaloketone derivative and then hydrolyzing the latter in the presence of a base, in particular to a process for producing a β-amino-α-hydroxycarboxylic acid derivative having the so-called erythro configuration. The "erythro configuration" herein indicates that the α-hydroxy and β-amino groups show the following relative arrangement:

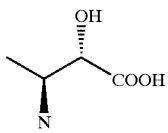

BACKGROUND ART

Among the so-far known processes for producing an optically active β-amino-α-hydroxycarboxylic acid derivative, there may be mentioned, for instance, the process comprising cyanizing an N-protected phenyl-alanial derivative and then hydrolyzing the resultant derivative ((1) Synthesis, 1989, page 709; (2) Journal of Medicinal Chemistry, vol. 37, page 2918, 1994; (3) Journal of Medicinal Chemistry, vol. 20, page 510, 1977).

However, the process comprising cyanizing an N-protected phenylalaninal derivative and then hydrolyzing the resultant derivative is not suited for the production of an erythro-form β-amino-α-hydroxy acid derivative since the stereoselectivity is of the so-called threo-selective type or almost no stereoselectivity is found. It has a problem in that the use of a strongly toxic cyanizing agent is required. Said threo configuration indicates a relative configuration opposite to the erythro configuration mentioned above.

A process is also known which comprises stereoselectively adding N-benzyl-α-phenethylamine to α,β-unsaturated esters in the manner of Michael addition, followed by hydroxylation (Synlett, vol. 10, page 731, 1993), for instance. However, it has a problem in that not less than equivalent amounts of the optically active amine and oxidizing agent have to be used.

SUMMARY OF THE INVENTION

Accordingly, it is an object of the present invention to provide a process for producing a β-amino-α-hydroxy acid derivative via steps feasible efficiently and industrially.

The gist of the present invention lies in that a β-amino-α-hydroxy acid derivative of the general formula (2):

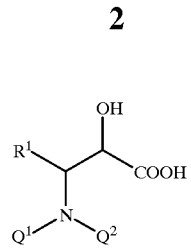

(wherein $R^1$ represents a substituted or unsubstituted alkyl group containing 1 to 20 carbon atoms, a substituted or unsubstituted aralkyl group containing 7 to 30 carbon atoms, or a substituted or unsubstituted aryl group containing 6 to 30 carbon atoms; $Q^1$ and $Q^2$ each independently represents a hydrogen atom or an amino-protecting group or $Q^1$ and $Q^2$ combinedly represent a phthaloyl group) is produced by hydrolyzing an α-amino-α', α'-dihaloketone derivative of the general formula (1):

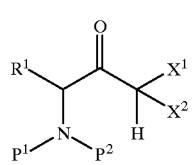

(wherein $R^1$ is as defined above; $X^1$ and $X^2$ each independently represents a halogen atom; $P^1$ and $P^2$ each independently represents a hydrogen atom or an amino-protecting group or $P^1$ and $P^2$ combinedly represent a phthaloyl group) in the presence of a base, followed by protecting the amino group or without protecting the same.

In another aspect, the gist of the present invention also consists in that the β-amino-α-hydroxy acid derivative of the general formula (2) given above is produced by treating an α-amino-α'-monohaloketone derivative of the general formula (3)

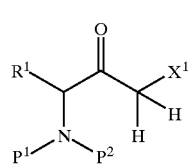

(wherein $R^1$ represents a substituted or unsubstituted alkyl group containing 1 to 20 carbon atoms, a substituted or unsubstituted aralkyl group containing 7 to 30 carbon atoms, or a substituted or unsubstituted aryl group containing 6 to 30 carbon atoms; $X^1$ represents a halogen atom; $P^1$ and $P^2$ each independently represents a hydrogen atom or an amino-protecting group or $P^1$ and $P^2$ combinedly represent a phthaloyl group) with a halogenating agent to give an α-amino-α', α'-dihaloketone derivative of the general formula (1) given above and then hydrolyzing the resultant derivative in the presence of a base, followed by protecting the amino group or without protecting the same.

The gist of the present invention further lies in that the β-amino-α-hydroxy acid derivative of the general formula (2) given above is produced by converting an α-amino acid derivative of the general formula (4):

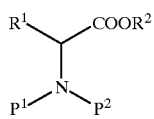
(4)

(wherein $R^1$ represents a substituted or unsubstituted alkyl group containing 1 to 20 carbon atoms, a substituted or unsubstituted aralkyl group containing 7 to 30 carbon atoms, or a substituted or unsubstituted aryl group containing 6 to 30 carbon atoms; $R^2$ represents a substituted or unsubstituted alkyl group containing 1 to 10 carbon atoms, a substituted or unsubstituted aralkyl group containing 6 to 15 carbon atoms, a substituted or unsubstituted aryl group containing 7 to 21 carbon atoms, or a hydrogen atom; $P^1$ and $P^2$ each independently represents a hydrogen atom or an amino-protecting group or $P^1$ and $P^2$ combinedly represent a phthaloyl group) to an α-amino-α'-monohaloketone derivative of the general formula (3) given above, further treating the resultant derivative with a halogenating agent to give an α-amino-α', α'-dihaloketone derivative of the general formula (1) given above and further hydrolyzing the same in the presence of a base, followed by protecting the amino group or without protecting the same.

DETAILED DESCRIPTION OF THE INVENTION

The present invention is now described in further detail.

The α-amino-α', α'-dihaloketone derivative, which is used in the practice of the present invention is a compound of the general formula (1) given above. The above-mentioned $R^1$ represents a substituted or unsubstituted alkyl group containing 1 to 20 carbon atoms, a substituted or unsubstituted aralkyl group containing 7 to 30 carbon atoms, or a substituted or unsubstituted aryl group containing 6 to 30 carbon atoms.

Said substituted or unsubstituted alkyl group containing 1 to 20 carbon atoms is not limited to any particular species but there may be mentioned, for example, methyl, ethyl, isopropyl, isobutyl, t-butyl, hydroxymethyl, 1-hydroxyethyl, mercaptomethyl, methylthiomethyl and the like.

The above-mentioned substituted or unsubstituted aralkyl group containing 7 to 30 carbon atoms is not limited to any particular species but includes, for example, benzyl, p-hydroxybenzyl, p-methoxybenzyl, phenylthiomethyl, α-phenethyl and the like.

The above-mentioned substituted or unsubstituted aryl group containing 6 to 30 carbon atoms is not limited to any particular species but includes, for example, phenyl, p-hydroxyphenyl, p-methoxyphenyl and the like.

The above-mentioned $R^1$ is the side chain of a common α-amino acid or the side chain of an α-amino acid derivative obtained by processing a common α-amino acid and may be any of substituted or unsubstituted alkyl groups containing 1 to 20 carbon atoms, substituted or unsubstituted aralkyl groups containing 7 to 30 carbon atoms and substituted or unsubstituted aryl groups containing 6 to 30 carbon atoms, without any particular limitation.

The above-mentioned $P^1$ and $P^2$ each independently represents a hydrogen atom or an amino-protecting group or $P^1$ and $P^2$ combinedly represent a phthaloyl group. The case in which each of $P^1$ and $P^2$ is a hydrogen atom is also included.

The amino-protecting group mentioned above is not limited to any particular species but there may be mentioned, for example, ethoxycarbonyl, methoxy-carbonyl, t-butoxycarbonyl, benzyloxycarbonyl, acetyl, trifluoroacetyl, benzyl, dibenzyl, tosyl, benzoyl, phthaloyl and the like, as described in Theodora W. Green: Protective Group In Organic Synthesis, 2nd Edition, JOHN WILEY & SONS, 1990, pages 309 to 384.

While the protective group mentioned above is selected taking into consideration of the reactivity and stereoselectivity in each step and other factors, there may be mentioned, as most preferred protective groups to be used in the synthesis of each compound represented by the general formula (4), (3), (1) or (2) mentioned above, ethoxycarbonyl, methoxycarbonyl, t-butoxycarbonyl, benzyloxycarbonyl and the like carbamate-forming groups, in particular ethoxycarbonyl. Carbamate-forming groups such as ethoxycarbonyl generally tend to preferentially give erythro stereoisomers, which are useful as an intermediate for HIV protease inhibitors, in the stage of the formation of compounds of general formula (2) from compounds of general formula (1).

The above-mentioned $X^1$ and $X^2$ each represents a halogen atom, such as fluorine, chlorine, bromine or iodine. It is preferred that each of $X^1$ and $X^2$ be chlorine.

As the above-mentioned α-amino-α', α'-dihalo-ketone derivative of general formula (1), there may be mentioned, for example, optically active ethyl (S)-(1-benzyl-3,3-dichloro-2-oxopropyl)carbamate, ethyl (R)-(1-benzyl-3,3-dichloro-2-oxopropyl)carbamate, methyl (S)-(1-benzyl-3,3-dichloro-2-oxopropyl)-carbamate, methyl (R)-(1-benzyl-3,3-dichloro-2-oxopropyl)carbamate, benzyl (S)-(1-benzyl-3,3-dichloro-2-oxopropyl)carbamate, benzyl (R)-(1-benzyl-3,3-dichloro-2-oxopropyl)carbamate, t-butyl (S)-(1-benzyl-3,3-dichloro-2-oxopropyl)carbamate, t-butyl (R)-(1-benzyl-3,3-dichloro-2-oxopropyl)-carbamate, ethyl (S)-(1-phenyl-3,3-dichloro-2-oxopropyl)carbamate, ethyl (R)-(1-phenyl-3,3-dichloro-2-oxopropyl)carbamate, ethyl (S)-(1-benzyl-3,3-dibromo-2-oxopropyl)carbamate, ethyl (R)-(1-benzyl-3,3-dibromo-2-oxopropyl)carbamate, ethyl (S)-(1-benzyl-3,3-dibromo-2-oxopropyl)carbamate, ethyl (S)-(1-phenyl-3,3-dichloro-2-oxopropyl)carbamate, N-(3,3-dichloro-1-methylacetonyl)phthalimide, 3-(N,N-dibenzylamino)-1,1-dichloro-2-oxo-4-phenylbutane and the like. Among these, some compounds, such as N-(3,3-dichloro-1-methylacetonyl)-phthalimide, are already known (Spisy Prirodoved. Fak. Univ. J. E. Purkyne Brne, (1968), No. 489, 1 to 7). However, an α-amino-α', α'-dichloroketone derivative of the general formula (5):

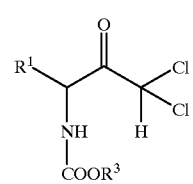
(5)

(wherein $R^1$ represents a substituted or unsubstituted alkyl group containing 1 to 20 carbon atoms, a substituted or unsubstituted aralkyl group containing 7 to 30 carbon atoms or a substituted or unsubstituted aryl group containing 6 to 30 carbon atoms and $R^3$ represents a substituted or unsubstituted alkyl group containing 1 to 10 carbon atoms, a substituted or unsubstituted aralkyl group containing 7 to 20 carbon atoms or a substituted or unsubstituted aryl group containing 6 to 20 carbon atoms), in particular an α-amino-α', α'-dichloroketone derivative of the general formula (6):

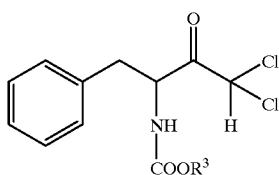

(6)

(wherein $R^3$ represents a substituted or unsubstituted alkyl group containing 1 to 10 carbon atoms, a substituted or unsubstituted aralkyl group containing 7 to 20 carbon atoms or a substituted or unsubstituted aryl group containing 6 to 20 carbon atoms) are novel compounds for which the method of production as well as the compounds themselves has not yet been described in the literature.

Referring to $R^3$ in the above general formula (5), the substituted or unsubstituted alkyl group containing 1 to 10 carbon atoms is, for example, methyl, ethyl, isopropyl, isobutyl, t-butyl or allyl, the substituted or unsubstituted aralkyl group containing 7 to 20 carbon atoms is benzyl, p-methoxybenzyl, p-nitrobenzyl or the like, and the substituted or unsubstituted aryl group containing 6 to 20 carbon atoms is phenyl, m-nitrophenyl or the like.

As the above-mentioned compound of general formula (5), there may be mentioned, for example, ethyl (S)-(1-benzyl-3,3-dichloro-2-oxopropyl)carbamate, ethyl (R)-(1-benzyl-3,3-dichloro-2 -oxopropyl)carbamate, methyl (S)-(1-benzyl-3,3-dichloro-2-oxopropyl)carbamate, methyl (R)-(1-benzyl-3,3-dichloro-2-oxopropyl)carbamate, benzyl (S)-(1-benzyl-3,3-dichloro-2-oxopropyl)carbamate, benzyl (R)-(1-benzyl-3,3-dichloro-2-oxopropyl)carbamate, t-butyl (S)-(1-benzyl-3,3-dichloro-2-oxopropyl)carbamate, t-butyl (R)-(1-benzyl-3,3-dichloro-2-oxopropyl)carbamate, ethyl (S)-(1-phenyl-3,3-dichloro-2-oxopropyl)carbamate, ethyl (R)-(1-phenyl-3,3-dichloro-2-oxopropyl)carbamate, ethyl (S)-(1-benzyl-3,3-dibromo-2-oxopropyl)carbamate, ethyl (R)-(1-benzyl-3,3-dibromo-2-oxopropyl)carbamate, ethyl (S)-(1-methyl-3,3-dichloro-2-oxopropyl)carbamate, ethyl (S)-(A-isobutyl-3,3-dichloro-2-oxopropyl)carbamate, ethyl (S)-(1-isopropyl-3,3-dichloro-2-oxopropyl)-carbamate, etc.

As the above-mentioned compound of general formula (6), there may be mentioned, for example, ethyl (S)-(1-benzyl-3,3-dichloro-2-oxopropyl)carbamate, ethyl (R)-(1-benzyl-3,3-dichloro-2-oxopropyl)carbamate, methyl (S)-(1-benzyl-3,3-dichloro-2-oxopropyl)carbamate, methyl (R)-(1-benzyl-3,3-dichloro-2-oxopropyl)carbamate, benzyl (S)-(1-benzyl-3,3-dichloro-2-oxopropyl)carbamate, benzyl (R)-(1-benzyl-3,3-dichloro-2-oxopropyl)carbamate, t-butyl (S)-(1-benzyl-3,3-dichloro-2-oxopropyl)carbamate, t-butyl (R)-(1-benzyl-3,3-dichloro-2-oxopropyl)carbamate, etc.

The hydrolysis reaction of the above-mentioned α-amino-α', α'-dihaloketone derivative in the presence of a base is preferably carried out in water or a mixed solvent composed of water and an organic solvent in the presence of a base.

Said organic solvent is not limited to any particular species but there may be mentioned, for example, of toluene, chlorobenzene, benzene, methylene chloride, methanol, ethanol, n-butanol, tetrahydrofuran, N,N-dimethylformamide and the like. Toluene, chlorobenzene and benzene are preferred, and toluene is more preferred.

Said base is not limited to any particular species but there may be mentioned, for example, of sodium hydroxide, potassium hydroxide, lithium hydroxide, barium hydroxide, magnesium hydroxide, calcium hydroxide, sodium carbonate, potassium carbonate, tetra-n-butylammonium hydroxide, tetramethylammonium hydroxide, trimethylbenzylammonium hydroxide, tetra-n-butylammonium hydroxide and the like. Sodium hydroxide is preferred, however.

While the reaction temperature in the above reaction may vary depending on the combination of substrate, solvent and base and other factors, the range of −30 to 100° C. is preferred and the range of −10 to 60° C. is more preferred. The reaction temperature influences the stereoselectivity and rate of reaction in the hydrolysis reaction. In the case of ethyl (S)-(1-benzyl-3,3-dichloro-2-oxopropyl)carbamate, for instance, lower temperatures tend to cause a decrease in the rate of reaction but an increase in erythro selectivity.

The reaction time may vary depending on the combination of substrate and base, the reaction temperature and other factors. Generally, however, 1 to 80 hours is preferred, and 3 to 20 hours is more preferred.

In the above-mentioned compound of general formula (2), $Q^1$ and $Q^2$ each independently represents a hydrogen atom or an amino-protecting group or $Q^1$ and $Q^2$ combinedly represent a phthaloyl group. When the compound of general formula (1) is hydrolyzed in the presence of a base, the amino group, if protected, may be deprotected or not be deprotected according to the combination of reaction conditions and protective group species. In the case of the hydrolysis of ethyl (S)-(1-benzyl-3,3-dichloro-2-oxopropyl) carbamate in an aqueous solution of sodium hydroxide, for instance, the amino deprotection tends to occur with ease. In this case, an oxazolidone derivative of the formula (7).

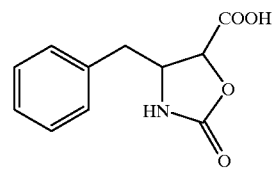

(7)

may be formed as a reaction intermediate. The resultant derivative, however, can be converted to a β-amino-α-hydroxy derivative of the general formula (2) given above in which $R^1$ is benzyl and $Q^1$ and $Q^2$ each is a hydrogen atom by further hydrolyzing under the reaction conditions. In cases where deprotection occurs in the reaction system, the product may be isolated in a protective group-free state or a new protective group may be introduced. Therefore, $Q^1$ and $Q^2$ each represents a hydrogen atom, or the same protective group as $P^1$ and $P^2$, or aprotective group newly introduced. Like $P^1$ and/or $P^2$, the group to be newly introduced is not limited to any particular species provided that it is a protective group generally used as an amino-protecting group. A t-butoxycarbonyl group is preferred, however.

In cases that a protective group is newly introduced, it is also possible, for example, to isolate the product of hydrolysis of the above-mentioned compound of general formula (1) by using a purification technique commonly used in isolating α-amino acids, such as crystallization or purification with an ion exchange resin, and then subject it to an amino group protection reaction, or subject the α-amino hydroxy acid in the aqueous layer, without isolation, to an amino group protection reaction.

When the above-mentioned compound of general formula (1) is subjected to said hydrolysis reaction, it is possible for the product to have any of four configurations. However, in cases where an optically active α-amino-α', α'-dihaloketone derivative such as ethyl (S)-(1-benzyl-3,3-dichloro-2-oxopropyl)-carbamate is used, it is surprising that racemization hardly proceeds and there is a tendency toward preferential formation of the erythro form of the two diastereomers that can possibly be formed. As a so-far known method of producing an α-hydroxy acid by alkali hydrolysis of an a-dihaloketone, there may be mentioned the method of producing mandelic acid using α-dichloroacetophenone (Organic Syntheses, Collective Volume 3, page 538), for instance. However, no technology has been known for producing an α-hydroxy acid derivative from an α', α'-dihaloketone having an optically active site in the a position of a carbonyl group with retaining the optical activity and stereoselectively.

The above-mentioned compound of general formula (1) can be produced by various methods. For instance, it can be produced by halogenating an α-amino-α'-monohaloketone derivative of the general formula (3):

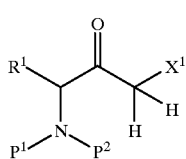

(3)

(wherein $R^1$, $X^1$, $P^1$ and $P^2$ are as defined above). The halogenating agent is not limited to any particular species but sulfuryl chloride or chlorine/carbon tetrachloride, for instance, may be used (Synthetic Communication, vol. 21, No. 1, page 111, 1991). From the viewpoint of economy and operability, among others, sulfuryl chloride is preferred.

The above-mentioned compound of general formula (3) can be produced by various methods. For instance, it can be produced by converting an α-amino acid derivative of the general formula (4):

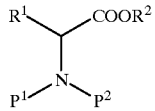

(4)

(wherein $R^2$, $P^1$ and $P^2$ are as defined above). As for the method of conversion, it can be produced, for instance, by reacting an ester derivative with the magnesium enolate of α-chloroacetic acid or the like (Japanese Patent Application Hei-07-273547).

(2S,3S)-3-[(t-butoxycarbonyl)amino]-2-hydroxy-4-phenylbutyric acid produced by the process of the present invention is a compound useful as an intermediate for the production of an HIV protease inhibitor (Japanese Kokai Publication Hei-05-170722).

BEST MODES FOR CARRYING OUT THE INVENTION

The following examples illustrate the present invention in further detail. They are, however, by no means limitative of the scope of the present invention.

EXAMPLE 1

Production of ethyl (S)-(1-benzyl-3-chloro-2-oxo-propyl)carbamate (I)

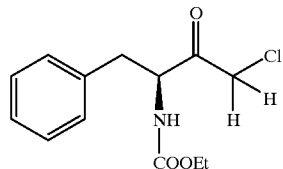

(I)

In a nitrogen gas atmosphere, a solution composed of (S)-N-(ethoxycarbonyl)phenylalanine methyl ester (35.0 g, 139 mmol), sodium monochloroacetate (24.2 g, 208 mmol), magnesium chloride (19.9 g, 208 mmol) and tetrahydrofuran (125 ml) was stirred at 40° C. for 3 hours (solution A). Separately, in a nitrogen atmosphere, diisopropylamine (65.0 g, 642 mmol) was added dropwise at 40° C. over 30 minutes to n-butylmagnesium chloride (2 M THF solution, 278 ml, 556 mmol) and the resulting mixture was further stirred at 40° C. for 2 hours (solution B). Solution B was added at about 10° C. (inside temperature) over about 30 minutes to solution A. After completion of the addition, the inside temperature was raised to 40° C. and stirring was continued for further 2 hours. Then, the reaction mixture was mixed with 900 ml of an ice-cooled mixed solution composed of 10% (w/v) aqueous solution of sulfuric acid and 550 ml of ethyl acetate with stirring. After thorough mixing, the mixture was allowed to separate into layers. The organic layer was washed in sequence with a saturated aqueous solution of sodium hydrogen carbonate (300 ml) and a saturated solution of sodium chloride (300 ml) and then dried over anhydrous sodium sulfate. The solvent was distilled off under reduced pressure, 30 ml of isopropanol was added to the residue, the mixture was heated to 60° C. to effect dissolution, 600 ml of hexane was then added, and the mixture was gradually cooled to 5° C. for allowing crystallization. The precipitate crystals were collected by filtration, washed with hexane and dried under reduced pressure to give 28.5 g of white needle crystals.

$^1$H NMR (400 MHz, CDCl$_3$): δ7.35 to 7.16 (m, 5H), 5.17 (d,1H), 4.75 (q, 1H), 4.17 to 4.08 (m, 2H), 4.00 to 3.96 (ds, 2H), 3.09 to 3.07 (m, 2H), 1.23 (t, 3H).

EXAMPLE 2

Production of ethyl (S)-(1-benzyl-3,3-dichloro-2-oxopropyl) carbamate (II)

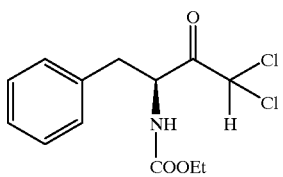

(II)

The compound (I) obtained in Example 1 (25.0 g, 92.7 mmol) was dissolved in ethyl acetate (250 ml), and sulfuryl chloride (38.8 g, 287 mmol) and p-toluenesulfonyl chloride monohydrate (1.8 g, 9.5 mmol) were added, and the mixture was stirred at 45° C. for 40 hours. The reaction mixture was cooled to room temperature and added to a solution composed of water (150 ml) and toluene (200 ml) while the pH was adjusted to about 3 with a 2 M aqueous solution of sodiumhydroxide. After thorough stirring, the organic layer was separated and concentrated to a volume of about 50 ml. That toluene solution was warmed to 60° C., hexane (300 ml) was added, and the mixture was gradually cooled to 5° C. for allowing crystallization. The crystals were collected by filtration, washed with hexane and dried under reduced pressure to give compound (II) (22.8 g, 75.0 mmol).

$^1$H NMR (400 MHz, CDCl$_3$): δ7.36 to 7.18 (m, 5H), 6.05 (s, 1H), 5.09 (d, 1H), 4.95 (q, 1H), 4.12 to 4.07 (q, 2H), 3.24 to 3.19 (dd, 1H), 3.07 to 3.02 (dd, 1H), 1.22 (t, 3H).

IR (KBr): 3450, 1746, 1690, 1551, 1266, 1048 cm$^{-1}$.

EXAMPLE 3

Production of (2RS,3S)-3-amino-2-hydroxy-4-phenyl-butyric acid (III)

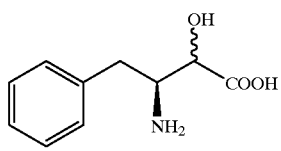

(III)

Toluene (120 ml) and a 2 M aqueous solution of sodium hydroxide (120 ml) were added to the compound (II) obtained in Example 2 (15 g, 49.3 mmol), and the mixture was stirred at 40° C. for 48 hours. The reaction mixture was allowed to cool to room temperature, and the aqueous layer was separated. This aqueous layer was adjusted to pH 7 and then passed through a column packed with 600 cm$^3$ of a synthetic adsorbent (Diaion SP207, product of Mitsubishi Chemical Corp.), the column was washed with water and elution was effected with 50% methanol. The eluate was concentrated to give the compound (III) (8.3 g, 86%).

Analysis of the compound (III) obtained by HPLC revealed that the proportion of the (2S,3S) isomer to the (2R,3S) isomer was 84:16.

For (2S,3S) isomer; $^1$H NMR (400 MHz, D$_2$O): δ7.25 to 7.13 (m, 5H), 4.10 (d, 1H), 3.66 (m, 1H), 2.79 to 2.76 (ddd, 1H), 2.70 to 2.64 (ddd, 1H).

For (2R,3S) isomer; $^1$H NMR (400 MHz, D$_2$O): δ7.25 to 7.13 (m, 5H), 3.87 (d, 1H), 3.61 (m, 1H), 3.00 to 2.95 (dd, 1H), 2.79 to 2.76 (ddd, 1H).

EXAMPLE 4

Production of (2RS,3S)-3-amino-2-hydroxy-4-phenyl-butyric acid (III)

The compound (II) (5.0 g, 16.4 mmol) was added to a 2 M aqueous solution of sodium hydroxide (50 ml) under ice cooling, and the mixture was stirred at 0° C. for 3 hours. Thereafter, the temperature was raised to 40° C. and stirring was continued for further 6 hours. The reaction mixture was allowed to cool to room temperature and then adjusted to pH 7 with 2 M aqueous hydrochloric acid. The thus-treated reaction mixture was passed through a 200 cm$^3$ column of a synthetic adsorbent (Diaion SP207, product of Mitsubishi Chemical Corp.), the column was washed with water and elution was effected with 50% aqueous methanol. The eluate was concentrated to give the compound (III) (2.6 g, 82%). Analysis of the compound (III) obtained by HPLC revealed that the proportion of the (2S,3S) isomer to the (2R,3S) isomer was 90:10.

EXAMPLE 5

Production of (2S,3S)-3-[(t-butoxycarbonyl)-amino]-2-hydroxy-4-phenylbutyric acid (IV)

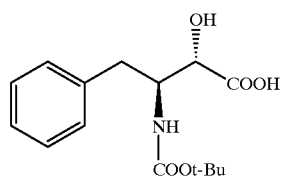

(IV)

The reaction was carried out in the same manner as in Example 3. The aqueous solution of (2RS,3S)-3-amino-2-hydroxy-4-phenylbutyric acid (III) (4.69 g, 24.0 mmol, erythro/threo=84/16) as obtained without synthetic adsorbent treatment was adjusted to pH 9 by adding 1 N aqueous NaOH and, after addition of 17.6 ml of THF, the mixed solution was cooled to an inside temperature not higher than 10° C.

After addition of sodium carbonate (3.35 g, 31.6 mmol) to the mixed solution, di-t-butyl dicarbonate (6.94 g, 31.8 mmol) was added dropwise. After completion of the dropping, the reaction mixture was stirred at room temperature for 8 hours. The reaction mixture was diluted with 120 ml of ethyl acetate and adjusted to pH 2 with 6 N hydrochloric acid, followed by phase separation.

The organic layer was washed with 50 ml of 10% citric acid and concentrated under reduced pressure to give a pale yellow solid. Acetonitrile (50 ml) was added and the mixture was heated to effect dissolution and then cooled to give 3.15 g (10.7 mmol, yield 44%) of the title compound as white crystals.

$^1$H NMR (400 MHz, DMSO-d$_6$): δ7.24 to 7.16 (m, 5H), 6.71 (d, 1H), 3.99 (d, 1H), 3.91 (m, 1H), 2.67 (d, 2H), 1.26 (s, 7H), 1.14 (s, 2H).

The result that the title compound obtained was in a (2S,3S) form was confirmed by converting to the corresponding methyl ester, followed by HPLC analysis on an optical dissolution column. Analysis: retention time in HPLC: (2S,3S) form 20.1 minutes, (2R,3R) form 21.9 minutes.

The HPLC analysis was performed under the following conditions:

Column: DAICEL Chiralcel ODH 4.6 mm ID×250 mm (Daicel Chemical Industries)

Eluant: hexane/i-propanol=98/2;

Rate of flow: 1.0 ml/min.;

Temperature: 40° C.

Detection wavelength: 210 nm.

EXAMPLE 6

Production of (2RS,3S)-3-[(p-toluenesulfonyl)-amino]-2-hydroxy-4-phenylbutyric acid (V)

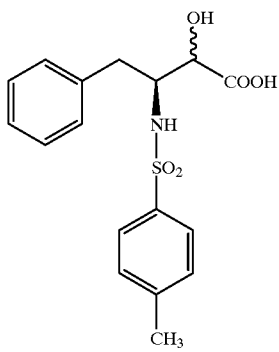

(V)

3-[(p-toluenesulfonyl)-amino]-1,1-dichloro-2-oxo-4-phenylbutane (55.6 mg, 0.1444 mmol) was dissolved in 3 ml of toluene, and an aqueous solution of sodium hydroxide (89 mg) in water (3 ml) was added while cooling the aqueous solution to 10° C. or below (inside temperature). After completion of the addition, the temperature of the reaction mixture was gradually raised to room temperature and the mixture was stirred for 19 hours.

Water (5 ml) and toluene (5 ml) were added to the reaction mixture, followed by phase separation. The aqueous layer was diluted with 10 ml of ethyl acetate and the pH was adjusted to 2 with 6 N hydrochloric acid, followed by phase separation. The organic layer was washed with 3 ml of 10% citric acid and concentrated under reduced pressure to give the title compound (V) as a roughly purified pale yellow oil (69 mg).

Analysis of the thus-obtained product (V) by HPLC revealed that the proportion of the (2S,3S) isomer to the (2R,3S) isomer was 70:30.

For (2S,3S) isomer; $^1$H NMR (400 MHz, CDCl$_3$): δ7.40 to 6.86 (m, 9H), 5.90 (d, 1H), 4.58 (d, 1H), 3.79 (m, 1H) 2.86 to 2.52 (m, 2H), 2.34 (s, 3H).

For (2R,3S) isomer; $^1$H NMR (400 MHz, CDCl$_3$): δ7.40 to 6.86 (m, 9H), 5.95 (d, 1H), 4.12 (d, 1H), 3.90 (m, 1H), 2.86 to 2.52 (m, 2H), 2.38 (s, 3H).

INDUSTRIAL APPLICABILITY

A (2S,3S)-3-amino-2-hydroxy-4-phenylbutyric acid derivative obtained by the production process of the present invention is a compound which is important as an intermediate for the production of medicinals such as antivirus agents and therefore, the present invention is very useful as a process for producing intermediates for the production of medicinals.

What is claimed is:

1. A method for crystallizing preferentially an erythro-isomer of α-hydroxy-β-amino compound presented by formula (2):

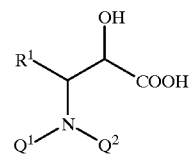

(2)

wherein $R^1$ represents a substituted or unsubstituted alkyl group containing 1 to 20 carbon atoms, a substituted or unsubstituted aralkyl group containing 7 to 30 carbon atoms, or a substituted or unsubstituted aryl group containing 6 to 30 carbon atoms; $Q^1$ and $Q^2$ each independently represents a hydrogen atom or an amino-protecting group or $Q^1$ and $Q^2$ combinedly represent a phthaloyl group with the proviso that $Q^1$ and $Q^2$ may not both be hydrogen, by using acetonitrile as solvent for the crystallization to eliminate the other stereoisomers.

2. The method of claim 1 wherein the other stereoisomers are diastereoisomers.

3. The method of claim 1 wherein said erythro-isomer is (α S, β S) isomer.

4. The method of claim 1 wherein said diastereoisomer is (α R, β S) isomer.

5. The method of claim 1 wherein said crystallization is cooling crystallization.

6. The method of claim 1 wherein $R^1$ is benzyl, $Q^1$ is hydrogen and $Q^2$ is t-butoxycarbonyl.

7. The method of claim 2 wherein said erythro-isomer is (α S, α S) isomer.

8. The method of claim 2 wherein said diastereoisomer is (α R, β S) isomer.

9. The method of claim 3 wherein said diastereoisomer is (α R, β S) isomer.

10. The method of claim 2 wherein said crystallization is cooling crystallization.

11. The method of claim 3 wherein said crystallization is cooling crystallization.

12. The method of claim 4 wherein said crystallization is cooling crystallization.

13. The method of claim 7 wherein said crystallization is cooling crystallization.

14. The method of claim 8 wherein said crystallization is cooling crystallization.

15. The method of claim 9 wherein said crystallization is cooling crystallization.

16. The method of claim 2 wherein $R^1$ is benzyl, $Q^1$ is hydrogen and $Q^2$ is t-butoxycarbonyl.

17. The method of claim 3 wherein $R^1$ is benzyl, $Q^1$ is hydrogen and $Q^2$ is t-butoxycarbonyl.

18. The method of claim 4 wherein $R^1$ is benzyl, $Q^1$ is hydrogen and $Q^2$ is t-butoxycarbonyl.

19. The method of claim 5 wherein $R^1$ is benzyl, $Q^1$ is hydrogen and $Q^2$ is t-butoxycarbonyl.

20. The method of claim 7 wherein $R^1$ is benzyl, $Q^1$ is hydrogen and $Q^2$ is t-butoxycarbonyl.

21. The method of claim 8 wherein $R^1$ is benzyl, $Q^1$ is hydrogen and $Q^2$ is t-butoxycarbonyl.

22. The method of claim 9 wherein $R^1$ is benzyl, $Q^1$ is hydrogen and $Q^2$ is t-butoxycarbonyl.

* * * * *